(12) United States Patent
Ferguson

(10) Patent No.: US 10,174,912 B1
(45) Date of Patent: Jan. 8, 2019

(54) FOCUSED LED HEADLAMP WITH IRIS ASSEMBLY

(71) Applicant: RIVERPOINT MEDICAL, LLC, Portland, OR (US)

(72) Inventor: John Thomas Ferguson, Portland, OR (US)

(73) Assignee: R IVERPOINT MEDICAL, LLC, Portland, OR (US)

(*) Notice: Subject to any disclaimer, the term of this patent is extended or adjusted under 35 U.S.C. 154(b) by 0 days.

(21) Appl. No.: 15/583,557

(22) Filed: May 1, 2017

(51) Int. Cl.
*F21V 21/084* (2006.01)
*F21V 13/02* (2006.01)
*F21V 5/04* (2006.01)
*F21V 11/10* (2006.01)
*F21V 14/08* (2006.01)
*F21V 29/70* (2015.01)
*F21V 5/00* (2018.01)
*F21V 23/00* (2015.01)
*A61B 90/30* (2016.01)
*A61B 90/50* (2016.01)
*F21Y 115/10* (2016.01)
*F21W 131/20* (2006.01)

(52) U.S. Cl.
CPC .............. *F21V 13/02* (2013.01); *A61B 90/30* (2016.02); *A61B 90/50* (2016.02); *F21V 5/008* (2013.01); *F21V 5/04* (2013.01); *F21V 11/10* (2013.01); *F21V 14/08* (2013.01); *F21V 21/084* (2013.01); *F21V 23/002* (2013.01); *F21V 29/70* (2015.01); *A61B 2090/309* (2016.02); *A61B 2090/502* (2016.02); *F21W 2131/20* (2013.01); *F21Y 2115/10* (2016.08)

(58) Field of Classification Search
CPC .... A61B 1/06; G02B 6/06; F21V 5/00; F21V 21/084; F21V 11/10; F21S 4/00; F21S 8/00
See application file for complete search history.

(56) References Cited

U.S. PATENT DOCUMENTS

| | | | | |
|---|---|---|---|---|
| 3,371,202 A | * | 2/1968 | Connors | .............. A61B 3/0008 362/281 |
| 3,480,836 A | * | 11/1969 | Aronstein | ............. H01L 23/538 174/252 |
| 4,104,709 A | * | 8/1978 | Kloots | .................... F21L 14/00 362/105 |

(Continued)

OTHER PUBLICATIONS

Cree, Cree XLamp XP-L LEDs, 2014-2015, Cree publication CLD-DS97 rev 2C.*

(Continued)

*Primary Examiner* — Ismael Negron
(74) *Attorney, Agent, or Firm* — Timothy E. Siegel Patent Law, PLLC; Timothy E. Siegel

(57) ABSTRACT

A medical headlamp that includes a tubular housing an electrical network electrically connected to an electrical conductor, a bare LED assembly electrically connected to the electrical network, an annular light block defining an aperture placed in front of the LED, and an optical assembly including at least a light focusing lens placed in front of the annular light block. A central beam of light from the LED passes through the aperture, and peripheral light from the LED is blocked by the light block such that the central light beam is focused by the optical assembly to create a beam of light having sharp edges.

22 Claims, 4 Drawing Sheets

(56) References Cited

U.S. PATENT DOCUMENTS

| | | | | |
|---|---|---|---|---|
| 4,491,622 | A * | 1/1985 | Butt | H05K 1/053 |
| | | | | 156/89.28 |
| 4,866,571 | A * | 9/1989 | Butt | H01L 23/047 |
| | | | | 361/717 |
| 5,014,159 | A * | 5/1991 | Butt | H01L 23/047 |
| | | | | 174/16.3 |
| 5,774,271 | A * | 6/1998 | Lagerway | F21L 14/00 |
| | | | | 359/649 |
| 5,857,767 | A * | 1/1999 | Hochstein | G09F 9/33 |
| | | | | 362/294 |
| 6,712,486 | B1 * | 3/2004 | Popovich | A47C 7/725 |
| | | | | 362/241 |
| 7,470,935 | B2 * | 12/2008 | Lee | H01L 33/486 |
| | | | | 257/98 |
| 7,572,031 | B2 * | 8/2009 | Schultz | H05K 1/0203 |
| | | | | 362/249.02 |
| 8,525,214 | B2 * | 9/2013 | Lin | H01L 21/486 |
| | | | | 257/707 |
| 9,091,428 | B2 | 7/2015 | Ferguson | |
| 9,234,653 | B2 * | 1/2016 | Ferguson | F21V 11/10 |
| 9,351,799 | B2 | 5/2016 | Ferguson | |
| 9,568,177 | B2 | 2/2017 | Ferguson | |
| 9,660,368 | B2 * | 5/2017 | Rathburn | H01R 12/7082 |
| 2006/0186906 | A1 * | 8/2006 | Bottoms | G01R 1/0483 |
| | | | | 324/755.05 |
| 2014/0334132 | A1 | 11/2014 | Ferguson | |
| 2014/0334159 | A1 | 11/2014 | Ferguson | |
| 2016/0123563 | A1 * | 5/2016 | Ferguson | F21V 21/084 |
| | | | | 362/277 |
| 2016/0207228 | A1 | 7/2016 | Ferguson | |

OTHER PUBLICATIONS

Cree, Cree XLamp XP-L LEDs, 2014, Cree Publication CLD-DS97 rev 0.*

Cree's New High-Intensity Class of LEDs More than Double Performance, www.led-professional.com, Jun. 1, 2015.*

* cited by examiner

FOCUSED LED HEADLAMP WITH IRIS ASSEMBLY

BACKGROUND

A medical headlamp is a device for which it is important to produce the maximum amount of light from the minimum amount of electricity. The advent of the light emitting diode (LED), which is a very efficient at turning electricity into light, with a minimum of heat produced, has permitted a great advance in the art. Still, heretofore, LEDs typically were available as part of a package that included a silicone dome lens over the LED. As the light had to pass through the silicone material of the dome lens, some efficiency was lost.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

In a first separate aspect, the invention may take the form of a medical headlamp that includes a tubular housing having a rear and a front and an electrical conductor, entering the housing. An electrical network is electrically connected to the electrical conductor and an LED assembly electrically connected to the electrical network. Also, an annular light block defines an aperture placed in front of the LED and a further optical assembly, including at least a light focusing lens is placed in front of the annular light block. Consequently, a central beam of light from the LED passes through the aperture, and peripheral light from the LED is blocked by the light block. The central light beam is focused by the further optical assembly, to create a beam of light having sharp edges, emanating from the headlamp. Finally, the LED assembly is substantially flat, not being capped by a lens having a radius of curvature of less than 1 mm. In various embodiments, the annular light block is fixed in dimension and the medical headlamp does not include any other annular light block; the annular light block is adjustable, to vary the size of the aperture and the housing includes an actuator for adjusting the adjustable annular light block. In various embodiments, the medical headlamp further includes a fixed dimension annular light block, placed in optical sequence to the adjustable light block; the light-focusing lens is made of glass. In various embodiments, the light-focusing lens is placed directly in front of and touches the annular light block. In various embodiments, the annular light block touches the LED; the prime lens is placed directly in front of and touches the annular light block; the annular light block is thinner than 100 mils. In various embodiments, the medical headlamp further includes headgear to permit the medical headlamp to be worn on a user's head; and in an additional optional embodiment, the housing has an interior surface and the electrical network is supported by a highly thermally conductive ceramic substrate that fits conformably in the housing, peripherally touching the interior surface of the housing, thereby providing a thermal pathway from the bare LED assembly to the housing.

In a second separate aspect, the invention may take the form of a medical headlamp that includes a tubular housing having a rear and a front and an electrical conductor, entering the housing. An electrical network is electrically connected to the electrical conductor and an LED assembly is electrically connected to the electrical network. Also, an iris assembly is placed directly in front of the LED assembly and includes an actuator and a toroidal housing. The housing defines an interior circumferential surface of the iris assembly, having a rear and a front, which define a width, therebetween. Further, the housing includes a set of iris blades that retract into and extend out of the housing at the interior circumferential surface to create a variable sized aperture, according to the actuator position. As such, the iris blades are not at the front of the circumferential surface, so that a margin is defined between the iris blades and the front, with the margin defining an interior space. Finally, a light-focusing lens is positioned at least partially in the interior space. In various embodiments, the medical headlamp further includes an exit lens, positioned in front of the light-focusing lens. In various embodiments, the LED assembly is a bare LED assembly; the housing includes an aft barrel, defining a slot over a portion of its circumference and the actuator of the iris assembly is a pin attached to a portion of the iris assembly that is moveable relative to the toroidal housing to cause the iris blades to extend and retract, and wherein the pin extends through the slot is attached to a rotatable collar set about the aft barrel; the medical headlamp further includes an annular light block interposed between the iris assembly and the LED assembly; and in an additional optional embodiment this annular light block is 0.25 mm (0.02") thick.

In a third separate aspect, the invention may take the form of a medical headlamp that includes a tubular housing having a rear and a front and an electrical conductor, entering the housing. An electrical network is electrically connected to the electrical conductor and an LED assembly is electrically connected to the electrical network. Also, an iris assembly is placed directly in front of the LED assembly and includes an actuator and a toroidal housing. The housing defines an interior circumferential surface of the iris assembly, having a rear and a front, which define a width, therebetween. Further, the housing includes a set of iris blades that retract into and extend out of the housing at the interior circumferential surface, to create a variable sized aperture, according to the actuator position. As such, the iris blades are not at the rear of the circumferential surface, so that a margin that is defined between the iris blades and the rear, with the margin defining an interior space. Finally, the iris assembly is positioned over the LED assembly so that the LED assembly is positioned at least partially in the interior space. In various embodiments, the LED assembly is positioned fully in the interior space. In one embodiment, the LED assembly is a bare assembly.

In a fourth separate aspect, the invention may take the form of a medical headlamp that is capable of emitting light from a front lens and includes a tubular housing, having a rear and a front, made of a thermally conductive metal and an electrical conductor, entering the housing. A ceramic substrate is conformally fit into the tubular housing and a light source is supported on the substrate. Further, an optical assembly, including the front lens, is positioned in front of the light source. Finally, the ceramic substrate is thermally conductive, thereby providing a thermal pathway from the light source to the tubular housing. In one embodiment, the ceramic substrate includes an electrical contact on its rear surface and the electrical conductor terminates in a contact bead that is pressed against the electrical contact, to form an electrical connection to the electrical network.

In addition to the exemplary aspects and embodiments described above, further aspects and embodiments will become apparent by reference to the drawings and by study of the following detailed descriptions.

BRIEF DESCRIPTION OF THE DRAWINGS

Exemplary embodiments are illustrated in referenced drawings. It is intended that the embodiments and figures disclosed herein are to be considered illustrative rather than restrictive.

DETAILED DESCRIPTION OF THE PREFERRED EMBODIMENTS

Definitions an LED assembly (or "package") is a light emitting diode (LED) or multiple light emitting diodes mounted closely together, plus immediately physically supporting elements, such as a substrate and electrical terminals. A "chip on board" or "COB" LED assembly is an LED assembly that is made up of multiple LED chips all bonded to a single substrate and typically powered through a single pair of terminals. A "substantially flat LED assembly" has no lens or is capped with a lens that has a radius of curvature of more than 1 mm. Stated slightly differently, a "relatively flat LED assembly" is an LED assembly that is not capped by a lens having a radius of curvature of less than 1 mm. A "bare LED assembly" is one which specifically does not include a light reflecting lens over the LED. Something that is "tubular" or a "tube" could have any closed shape in cross-section, such as a circle, a rectangle or a hexagon, for example.

Figure 1:
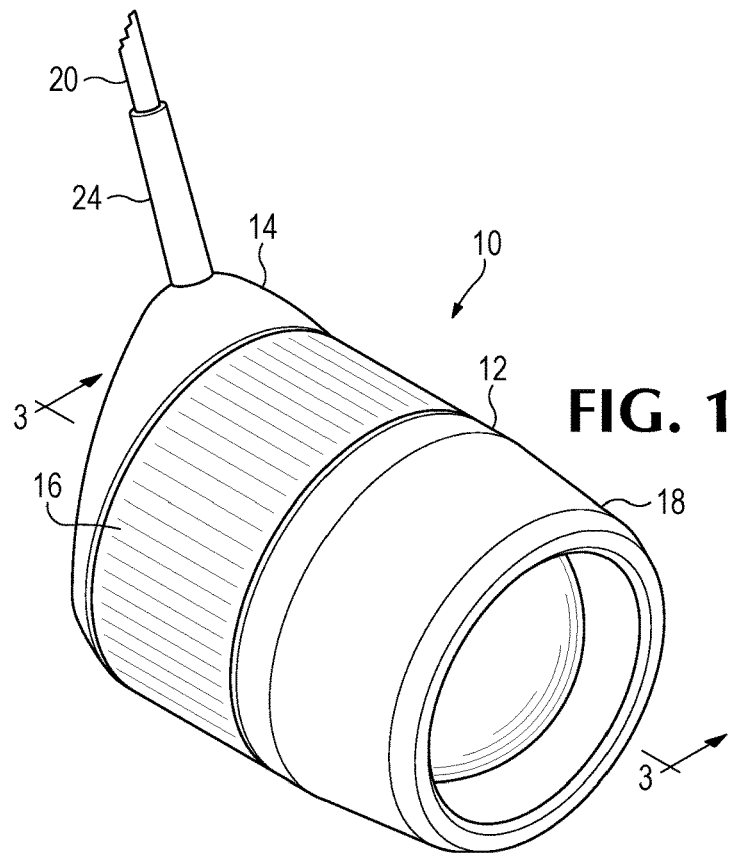
FIG. 1 is an isometric rendering of a medical headlamp, according to the present invention.
Figure 2:
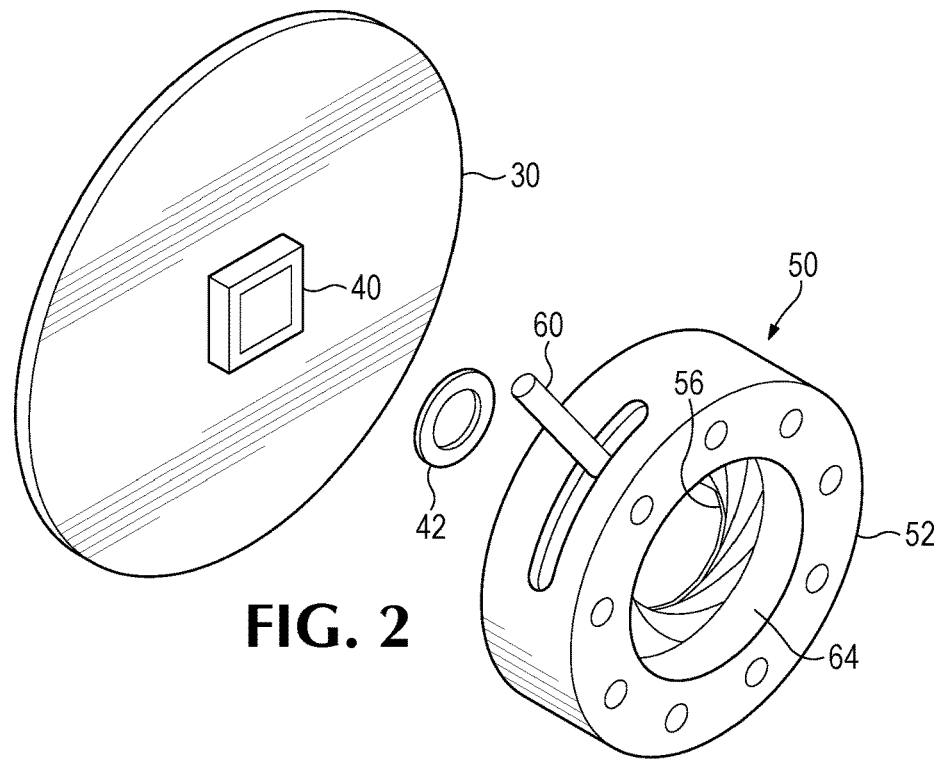
FIG. 2 is an isometric view of some interior elements of the medical headlamp of FIG. 1.

In a first preferred embodiment, a medical headlamp 10 (also referred to as a bezel) includes a housing 12, made up of an aft barrel 14, a rotating adjustment collar 16 and an exit lens holder 18. A wire 20, terminating in a contact bead 22 (FIG. 3) is held within a boot 24 that extends through an opening 26 (FIG. 3) in the aft barrel 14. A ceramic substrate 30 (FIG. 2) supports an electrical circuit (not shown) that powers an LED assembly 40, which in one embodiment is a COB LED assembly. Ceramic substrate 30 includes an electrical contact pad (not shown) on its rear surface, which during assembly is pushed into contact bead 22, partially crushing it and establishing a robust electrical connection. Details of this process will be described further, below. For ease of presentation only one contact bead 22 has been shown, but an anode and cathode bead 22 are used in a preferred embodiment, separated by a "Y" structure in the boot 24 to keep the two contact beads separated during and after placement, and to prevent wire 20 from being accidentally torn out of housing 12.

Figure 3:
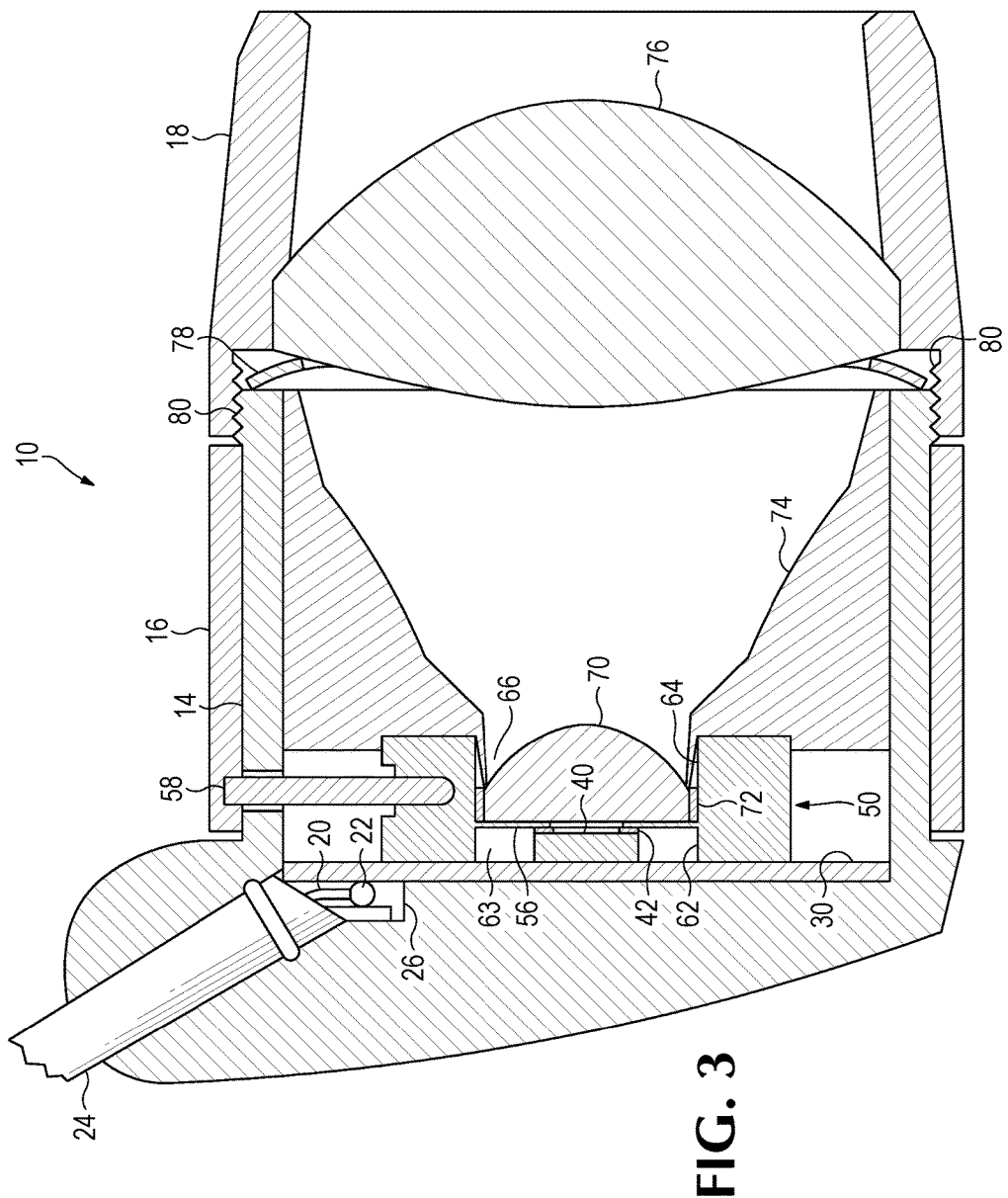
FIG. 3 is a sectional view, taken along line 3-3 of FIG. 1.
Figure 4:
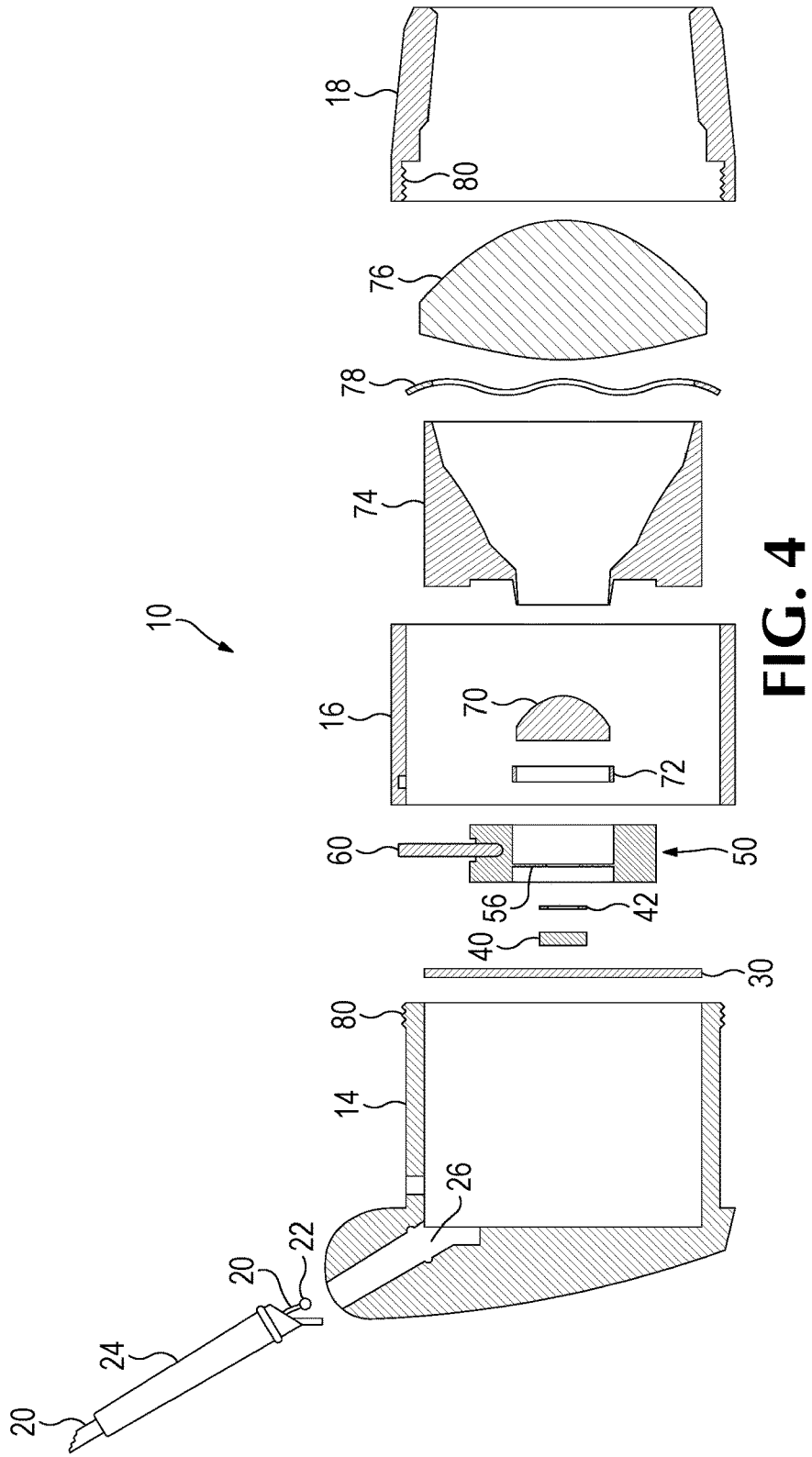
FIG. 4 is an exploded sectional view, taken along line 3-3 of FIG. 1.

A light block 42 is either positioned directly on the surface of LED 40 or held directly in front of it. In varying embodiments, light block 42 is 25 microns (1 mil) to 500 microns (0.02") thick. In front of the light block there is an iris assembly 50 (which may also be termed "an adjustable light block") having a toroidal housing 52, and a set of iris blades 56 that retract into and extend out of the housing into the space defined by the toroidal housing, to create a variable sized aperture, according the position of an actuator 58 (FIG. 3).

The iris blades are not at the rear or the front of the circumferential surface so that a rear margin and a front margin is defined between the iris blades 56 and the rear and the front, respectively, with the rear margin 62 defining a rear interior space 63 and the front margin 64 defining a front interior space 66. The iris assembly 50 is positioned so that LED 40 fits in the rear interior space. In one preferred embodiment, LED assembly 40 includes a lens that extends into the aperture between the iris blades 56. The actuator 58 is in the form of a pin 60 (FIG. 2) and the rotatable collar 16, joined together. The pin 60 extends through a circumferential slot in the aft barrel 14 to connect to collar 16, which is rotated to adjust the size of the iris opening.

A prime lens 70 (which may also be termed a light-focusing lens) is fitted into the front interior space 66, with a heat-shrink PTFE collar 72 to facilitate insertion and smooth any discrepancies in the fit. Forward of lens 70, a lens cone 74 reflects any stray light forward. Finally, an exit lens 76 is held in the exit lens holder 18, against a circular spring 78, which is interposed between exit lens 76 and lens cone 74. Exit lens holder 18 is threaded onto aft barrel 14 at threads 80. In an alternative embodiment, prime lens 70 is interposed between the iris blades. In an additional alternative embodiment, exit lens 76 and prime lens 70 are replaced by a single lens, that combines the functions of both lenses.

Two features of the assembly of headlamp 10, facilitate the efficient manufacture of a robust product. As noted above, the contact bead 22 is held in place boot 24 and ceramic substrate 30. During assembly, as exit lens holder 18 is threaded onto aft barrel 14 at threads 80, lens cone 74 is pressed against substrate 30, which eventually crushes bead 22, forming a robust contact with the contact pad on the rear of substrate 30.

In addition, in systems using an iris, a time-consuming task of adjusting the maximum size aperture created by the withdrawal of blades 56 into housing 52, if often faced by assembly personnel. At some point, if the blades are withdrawn too far, the aperture they create deviates far from a perfect circle, creating an irregular spot of light, that gives the impression that the device is cheaply made. To avoid this problem, the iris is adjusted during assembly to set a maximum aperture size. But in the use of device 10, the light block 42 sets the appearance of the light spot when the iris blades 56 are withdrawn far enough to be outside the beam created by light block 42. Accordingly, there is no need to set a maximum aperture size, thereby easing the task of assembly.

The headlamp described above can generally produce more light per unit of power applied to it than previously available headlamps. It is also more compact, thereby reducing total headlamp weight. In a preferred embodiment, the headlamp produces between 130-140 lumens per watt and runs between three and four Watts with a weight ranging from two to four ounces. In one preferred embodiment, bare LED assembly 40 is a Cree® XP-L High Intensity LED, chosen from the different options listed in Table 1, below:

TABLE 1

| Kit | Chromaticity CCT | Code | Minimum Luminous Flux (lm) @ 1050 mA | | Order Codes | |
|-----|------|------|------|------|------|------|
| | | | Flux (lm) @ 85° C. | Flux (lm) @ 25° C.* | 65 CRI Typical | 70 CRI Minimum |
| 51 | 6200K | V2 | 400 | 446 | XPLAWT-H0-0000V2051 | XPLAWT-H0-000BV2051 |
| | | U6 | 380 | 424 | XPLAWT-H0-0000U6051 | XPLAWT-H0-000BU6051 |
| | | U5 | 360 | 401 | XPLAWT-H0-0000U5051 | XPLAWT-H0-000BU5051 |
| 53 | 6000K | V2 | 400 | 446 | XPLAWT-H0-0000V2053 | XPLAWT-H0-000BV2053 |
| | | U6 | 380 | 424 | XPLAWT-H0-0000U6053 | XPLAWT-H0-000BU6053 |
| | | U5 | 360 | 401 | XPLAWT-H0-0000U5053 | XPLAWT-H0-000BU5053 |
| 50 | 6200K | V2 | 400 | 446 | XPLAWT-H0-0000V2050 | XPLAWT-H0-000BV2050 |
| | | U6 | 380 | 424 | XPLAWT-H0-0000U6050 | XPLAWT-H0-000BU6050 |
| | | U5 | 360 | 401 | XPLAWT-H0-0000U5050 | XPLAWT-H0-000BU5050 |
| E1 | 6500K | V2 | 400 | 446 | XPLAWT-H0-0000V20E1 | XPLAWT-H0-000BV20E1 |
| | | U6 | 380 | 424 | XPLAWT-H0-0000U60E1 | XPLAWT-H0-000BU60E1 |
| | | U5 | 360 | 401 | XPLAWT-H0-0000U50E1 | XPLAWT-H0-000BU50E1 |
| E2 | 5700K | V2 | 400 | 446 | XPLAWT-H0-0000V20E2 | XPLAWT-H0-000BV20E2 |
| | | U6 | 380 | 424 | XPLAWT-H0-0000U60E2 | XPLAWT-H0-000BU60E2 |
| | | U5 | 360 | 401 | XPLAWT-H0-0000U50E2 | XPLAWT-H0-000BU50E2 |

In one embodiment, headlamp 10 is connected to a headband assembly, such as that shown and described in U.S. Pat. No. 9,351,799, which is owned by the assignee of this application.

Figure 5:
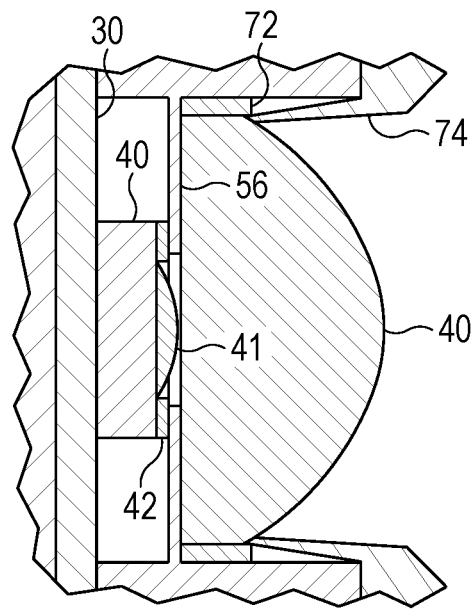
FIG. 5 is a sectional view of a distinguishing detail of an alternative embodiment, taken in plane 3-3 of FIG. 1.
Figure 6:
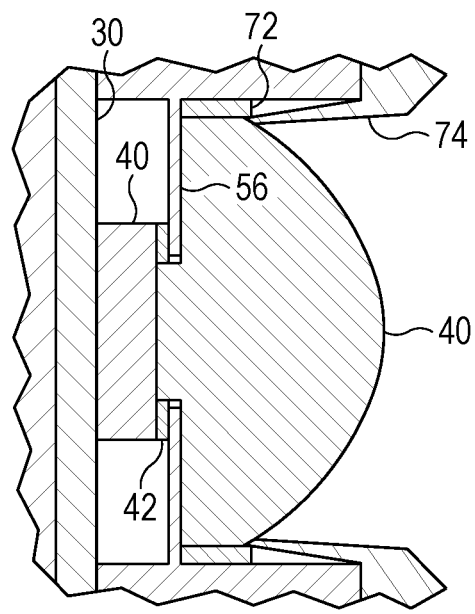
FIG. 6 is a sectional view of a distinguishing detail of an additional alternative embodiment, taken in plane 3-3 of FIG. 1

Referring now to FIG. 5, in one embodiment, LED assembly 40 includes a shallow lens 41, having radius of curvature of greater than 1 mm and that extends into the aperture defined by iris blades 56. In an additional preferred embodiment, light block 42 is absent. Referring to FIG. 6, in one embodiment, lens 40 extends through the aperture defined by iris blades 56 and light block 42. In alternative embodiments, light block 42 is absent. In another alternative, light block 42 is present, but lens 40 does not extend through the aperture defined by light block 42, or only extends part way through.

While a number of exemplary aspects and embodiments have been discussed above, those possessed of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

The invention claimed is:

1. A headlamp, comprising:
(a) a tubular housing having a rear and a front;
(b) an electrical conductor, entering said housing;
(c) an electrical network, electrically connected to said electrical conductor;
(d) an LED assembly, including a lens, electrically connected to said electrical network, and including at least one LED;
(e) an annular light block defining an aperture placed in front of said LED, wherein said annular light block is adjustable, to vary the size of said aperture and said housing includes an actuator for adjusting said adjustable annular light block, and wherein said lens of said LED assembly protrudes into said aperture;
(f) an optical assembly, including at least a light-focusing lens placed in front of the annular light block;
(g) whereby, a central beam of light from said LED passes through said aperture, and peripheral light from said LED is blocked by said light block, said central light beam is focused by said further optical assembly, to create a beam of light having sharp edges emanating from said headlamp;
(h) wherein said LED assembly is a substantially flat LED assembly.

2. The headlamp of claim 1, further including a fixed dimension annular light block such that said adjustable light block is situated between, and in optical sequence with said fixed dimension annular light block and said optical assembly.

3. The headlamp of claim 1, wherein said annular light block is thinner than 100 mils.

4. The headlamp of claim 1, further including headgear to permit said headlamp to be worn on a user's head.

5. The headlamp of claim 1, wherein said housing has an interior surface and said electrical network is supported by a highly thermally conductive ceramic substrate that fits conformably in said housing, peripherally touching said interior surface of said housing, thereby providing a thermal pathway from said LED assembly to said housing.

6. The headlamp of claim 1, wherein said LED assembly is a COB LED assembly.

7. The headlamp of claim 1, wherein said light-focusing lens is made of glass.

8. The headlamp of claim 7, wherein said light-focusing lens is placed directly in front of and touches said annular light block.

9. A headlamp, comprising:
(a) a tubular housing having a rear and a front;
(b) an electrical conductor, entering said housing;
(c) an electrical network, electrically connected to said electrical conductor;
(d) an LED assembly electrically connected to said electrical network, and including at least one LED;
(e) an annular light block defining an aperture placed in front of said LED, wherein said annular light block is adjustable, to vary the size of said aperture and said housing includes an actuator for adjusting said adjustable annular light block;
(f) an optical assembly, including at least a light-focusing lens placed in front of the annular light block, wherein said light-focusing lens is shaped to include a protrusion, and wherein said protrusion extends into said aperture;

(g) whereby, a central beam of light from said LED passes through said aperture, and peripheral light from said LED is blocked by said light block, said central light beam is focused by said further optical assembly, to create a beam of light having sharp edges emanating from said headlamp;

(h) wherein said LED assembly is a substantially flat LED assembly.

10. The headlamp of claim 9, wherein said annular light block touches said LED.

11. The headlamp of claim 9, wherein said LED assembly is a bare LED assembly, that includes no refractive lens.

12. A headlamp, comprising:
(a) a tubular housing having a rear and a front;
(b) an electrical conductor, entering said housing;
(c) an electrical network, electrically connected to said electrical conductor;
(d) an LED assembly, electrically connected to said electrical network;
(e) an iris assembly, placed directly in front of said LED assembly, having:
    (i) an actuator; and
    (ii) a toroidal housing, defining an interior circumferential surface having a rear and a front, which define a width, therebetween, and further including a set of iris blades that retract into and extend out of said toroidal housing at said interior circumferential surface, to create a variable sized aperture, according to actuator position, and wherein said iris blades are not at said front of said circumferential surface so that a margin is defined between said iris blades and said front, said margin defining an interior space; and
(f) a light-focusing lens, positioned at least partially in said interior space.

13. The headlamp of claim 12, further including an exit lens, positioned in front of said light-focusing lens.

14. The headlamp of claim 12, wherein said LED assembly is a bare LED assembly.

15. The headlamp of claim 12, wherein said LED assembly is a COB LED assembly.

16. The headlamp of claim 12, wherein said tubular housing includes an aft barrel, defining a slot over a portion of its circumference and said actuator of said iris assembly is a pin attached to a portion of said iris assembly that is moveable relative to said toroidal housing to cause said iris blades to extend and retract, and wherein said pin extends through said slot is attached to a rotatable collar set about said aft barrel.

17. The headlamp of claim 12, further including an annular light block interposed between said iris assembly and said LED assembly.

18. The headlamp of claim 17, wherein said annular light block is 0.25 mm (0.01") thick.

19. A headlamp, comprising:
(a) a tubular housing having a rear and a front;
(b) an electrical conductor, entering said housing;
(c) an electrical network, electrically connected to said electrical conductor;
(d) an LED assembly, electrically connected to said electrical network;
(e) an iris assembly, placed directly in front of said LED assembly, having:
    (i) an actuator; and
    (ii) a toroidal housing, defining an interior circumferential surface having a rear and a front, which define a width, therebetween, and further including a set of iris blades that retract into and extend out of said toroidal housing at said interior circumferential surface, to create a variable sized aperture, according to actuator position, and wherein said iris blades are not at said rear of said circumferential surface so that a margin is defined between said iris blades and said rear, said margin defining an interior space; and
(f) said iris assembly positioned over said LED assembly so that said LED assembly is positioned at least partially in said interior space.

20. The headlamp of claim 19, wherein said LED assembly is positioned fully in said interior space.

21. The headlamp of claim 19, wherein said LED assembly is a bare LED assembly.

22. A headlamp, capable of emitting light from a front lens, and comprising:
(a) a tubular housing having a rear and a front, and being made of a thermally conductive metal;
(b) an electrical conductor, entering said housing;
(c) a ceramic substrate conformally fit into said tubular housing; and
(d) a light source supported on said substrate;
(e) an optical assembly, including said front lens, positioned in front of said light source;
(f) wherein said ceramic substrate is thermally conductive, thereby providing a thermal pathway from said light source to said tubular housing; and
(g) wherein said ceramic substrate includes an electrical contact on its rear surface and said electrical conductor terminates in a contact bead that is pressed against said electrical contact to form an electrical connection to said electrical network.

\* \* \* \* \*